United States Patent
Pheiffer et al.

(10) Patent No.: US 10,716,457 B2
(45) Date of Patent: Jul. 21, 2020

(54) METHOD AND SYSTEM FOR CALCULATING RESECTED TISSUE VOLUME FROM 2D/2.5D INTRAOPERATIVE IMAGE DATA

(71) Applicant: Siemens Aktiengesellschaft, Munich (DE)

(72) Inventors: Thomas Pheiffer, Langhorne, PA (US); Stefan Kluckner, Princeton, NJ (US); Ali Kamen, Skillman, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1191 days.

(21) Appl. No.: 14/882,485

(22) Filed: Oct. 14, 2015

(65) Prior Publication Data
US 2017/0105601 A1 Apr. 20, 2017

(51) Int. Cl.
| | |
|---|---|
| *A61B 1/00* | (2006.01) |
| *A61B 34/30* | (2016.01) |
| *G06T 17/10* | (2006.01) |
| *G06T 7/55* | (2017.01) |
| *G06T 7/62* | (2017.01) |
| *A61B 1/04* | (2006.01) |

(52) U.S. Cl.
CPC .......... *A61B 1/00009* (2013.01); *A61B 1/04* (2013.01); *A61B 34/30* (2016.02); *G06T 7/55* (2017.01); *G06T 7/62* (2017.01); *G06T 17/10* (2013.01); *G06T 2207/10016* (2013.01); *G06T 2207/10028* (2013.01); *G06T 2207/10068* (2013.01); *G06T 2207/30024* (2013.01); *G06T 2207/30096* (2013.01)

(58) Field of Classification Search
None
See application file for complete search history.

(56) References Cited

U.S. PATENT DOCUMENTS

2011/0211754 A1* 9/2011 Litvak ............... G06K 9/00375
382/165
2012/0307010 A1 12/2012 Avram
(Continued)

OTHER PUBLICATIONS

"Fast and Accurate Computation of Polyhedral Mass Properties" by B. Mirtich. Journal of Graphics Tools. vol. 1 1996—Issue 2. pp. 31-50.*

(Continued)

*Primary Examiner* — Jeffrey G Hoekstra
*Assistant Examiner* — Jason M Ip

(57) ABSTRACT

A method and system for calculating a volume of resected tissue from a stream of intraoperative images is disclosed. A stream of 2D/2.5D intraoperative images of resected tissue of a patient is received. The 2D/2.5D intraoperative images in the stream are acquired at different angles with respect to the resected tissue. A resected tissue surface is segmented in each of the 2D/2.5D intraoperative images. The segmented resected tissue surfaces are stitched to generate a 3D point cloud representation of the resected tissue surface. A 3D mesh representation of the resected tissue surface is generated from the 3D point cloud representation of the resected tissue surface. The volume of the resected tissue is calculated from the 3D mesh representation of the resected tissue surface.

25 Claims, 3 Drawing Sheets

(56) References Cited

U.S. PATENT DOCUMENTS

| | | | | |
|---|---|---|---|---|
| 2013/0060146 | A1* | 3/2013 | Yang | A61B 5/055 |
| | | | | 600/476 |
| 2014/0330288 | A1* | 11/2014 | Date | A61B 34/30 |
| | | | | 606/130 |

OTHER PUBLICATIONS

"From Segmented Medical Images to Surface and Volume Meshes, Using Existing Tools and Algorithms" by C. Lobos et al. Conference: Proceedings of the VI International Conference on Adaptive Modeling and Simulation, ADMOS 2013.*

"Towards Detection and Localization of Instruments in Minimally Invasive Surgery" by M. Allan et al. IEEE Trans on Biomedical Engineering. vol. 60, No. 4. pp. 1050-1058. Apr. 2013.*

Jean-Nicolas Vauthey, MD. et al. "Standardized Measurement of the Future Liver Remnant Prior to Extended Liver Resection: Methodology and Clinical Associations" (8-pages).

Mathew M. Grabowski, B.S, et al. "Residual Tumor Volume Versus Extent of Resection: Predictors of Survival After Surgery for Glioblastoma"; Brain Tumor and Neuro-Oncology Center and Department of Neurosurgery, and Department of Quantitative Health Sciences, Cleveland, OH (9 pages).

Michael Kazhdan et al. "Poisson Surface Reconstruction"; Johns Hopkins University, Baltimore MD. (10 pages).

Abdalmajeid M. Alyassin et al. "Evaluation of New Algorithms for the Interactive Measurement of Surface Area and Volume"; Department of Radiology and Research Imaging Center, The University of Texas Health Science Center at San Antonio, TX 78284-6240 (12 pages).

Prankl Johann et al: "RGB-D object modelling for object recognition and tracking", 2015 IEEE/RSJ International Conference on Intelligent Robots and Systems (IROS), IEEE, Sep. 28, 2015 (Sep. 28, 2015), pp. 96-103, XP032831581; 2015.

L. Maier-Hein et al: "Optical techniques for 3D surface reconstruction in computer-assisted laparoscopic surgery", Medical Image Analysis, vol. 17, No. 8, May 3, 2013 (May 3, 2013), pp. 974-996, XP055249579; 2013.

Li Zhi-Cheng et al: "Accurate kidney surface reconstruction from 3D ultrasonography for volume assessment: First clinical evaluation", 2015 37th Annual International Conference of the IEEE Engineering in Medicine and Biology Society (EMBC), IEEE, Aug. 25, 2015 (Aug. 25, 2015), pp. 2981-2984, XP032810795; 2015.

Wan Yan et al: "Anthropometric techniques based on kinect 3D scanning", Proceedings 2013 International Conference on Mechatronic Sciences, Electric Engineering and Computer (MEC), IEEE, Dec. 20, 2013 (Dec. 20, 2013), pp. 1292-1296, XP032634625; 2013.

PCT International Search Report dated Dec. 23, 2016 corresponding to PCT International Application No. PCT/US2016/056734 filed Oct. 13, 2016 (16 pages).

Tobert et al., "Surgeon Assessment of Renal Preservation with Partial Nephrectomy Provides Information Comparable to Measurement of Volume Preservation with 3-Dimensional Image Analysis," The Journal of Urology, 2014, vol. 191, pp. 1218-1224.

* cited by examiner

METHOD AND SYSTEM FOR CALCULATING RESECTED TISSUE VOLUME FROM 2D/2.5D INTRAOPERATIVE IMAGE DATA

BACKGROUND OF THE INVENTION

The present invention relates to estimating the volume of tissue resected in a surgical intervention, and more particularly, to estimating the volume of the resected tissue from 2D/2.5D intraoperative image data.

Surgical interventions often involve resection and removal of tissue from a patient, especially for the removal of tumors in cancer patients. In such cases, an accurate understanding of the extent of tissue to be removed is critical. For example, patient survival outcomes in neurosurgery have been linked to residual tumor volume after resection, liver function is correlated with the remaining viable liver tissue after tumor resection in hepatic surgery, and renal function after partial nephrectomy has been linked to the kidney volume preserved. Volume measurements of the surgical target are often made on pre-operative images, such as computed tomography (CT) or magnetic resonance (MR) images, which help guide clinical decision making. Corresponding volume measurements are not typically performed intraoperatively for most procedures, likely because performing such volume measurements would be too disruptive to the surgical workflow.

BRIEF SUMMARY OF THE INVENTION

The present invention provides a method and system for calculating the volume of resected tissue using intraoperative image data, such as laparoscopic or endoscopic image streams. Embodiments of the present invention create a 3D model of the tissue of interest by stitching together sequences of 2D/2.5D intraoperative images of resected tissue removed during a surgical intervention. The reconstructed model represents a physical measurement of the tissue geometry which is used to calculate the volume of resected tissue.

In one embodiment of the present invention, stream of 2D/2.5D intraoperative images of resected tissue of a patient that has been removed from surrounding tissue of the patient is received. The stream of 2D/2.5D intraoperative images comprises a plurality of 2D/2.5 images acquired at different angles with respect to the resected tissue. A resected tissue surface is segmented in each of the plurality of 2D/2.5D intraoperative images. The segmented resected tissue surfaces are stitched to generate a 3D point cloud representation of the resected tissue surface. A 3D mesh representation of the resected tissue surface is generated from the 3D point cloud representation of the resected tissue surface. The volume of the resected tissue is calculated from the 3D mesh representation of the resected tissue surface.

These and other advantages of the invention will be apparent to those of ordinary skill in the art by reference to the following detailed description and the accompanying drawings.

DETAILED DESCRIPTION

The present invention relates to a method and system for calculating the volume of resected tissue in a surgical intervention from intraoperative image data, such as laparoscopic or endoscopic image data. Embodiments of the present invention are described herein to give a visual understanding of the method for calculating the volume of resected tissue from intraoperative image data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

There are an increasing number of minimally invasive surgical procedures being performed that utilize cameras such as endoscopes or laparoscopes. Embodiments of the present invention use such intraoperative imaging to acquire continuous surface measurements of resected tissue removed during a surgical procedure. Using 2D/2.5D depth data, surface measurements form multiple intraoperative images (e.g., multiple frames of an endoscopic or laparoscopic video) are combined to generate a 3D model of the resected tissue. The 3D model represents the 3D geometry of the resected tissue and provides a measurement of the volume of the resected tissue. The methods described herein can be implemented with interactive response times, and thus can be performed in real-time or near real-time during a surgical procedure. Is to be understood that the terms "laparoscopic image" and "endoscopic image" are used interchangeably herein and the term "intra-operative image" refers to any medical image data acquired during a surgical procedure or intervention, including laparoscopic images and endoscopic images.

Figure 1:
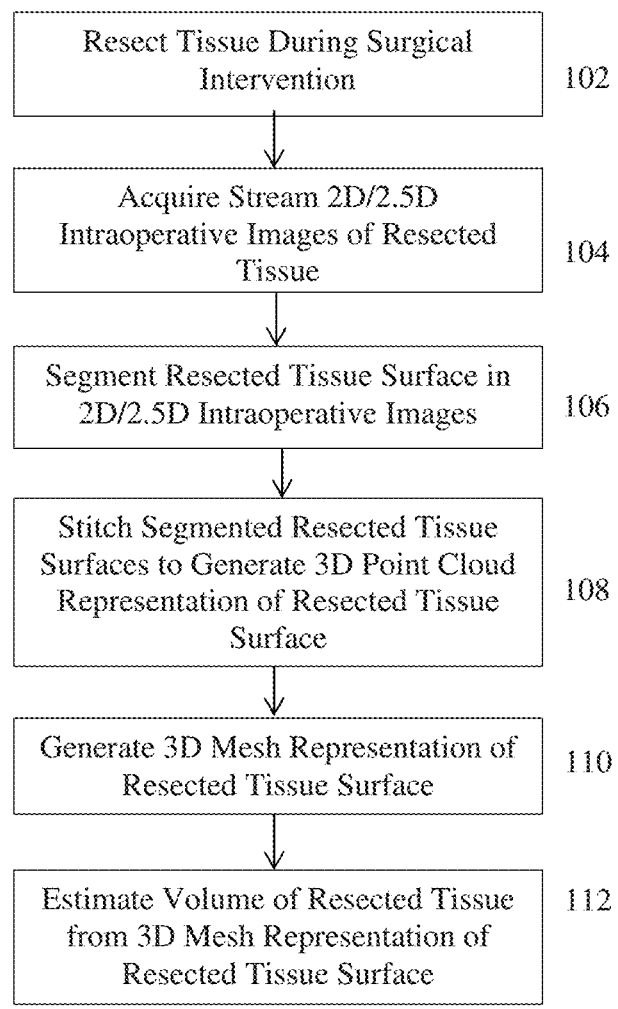
FIG. 1 illustrates a method for calculating a volume of resected tissue according to embodiment of the present invention.

FIG. 1 illustrates a method for calculating a volume of resected tissue according to embodiment of the present invention. The method of FIG. 1 can be used to calculate the volume of resected tissue in a surgical intervention from intraoperative image data. The method of FIG. 1 transforms intraoperative image data to generate a 3D model of the resected tissue and calculated the volume of the resected tissue from the generated volume.

Figure 2:
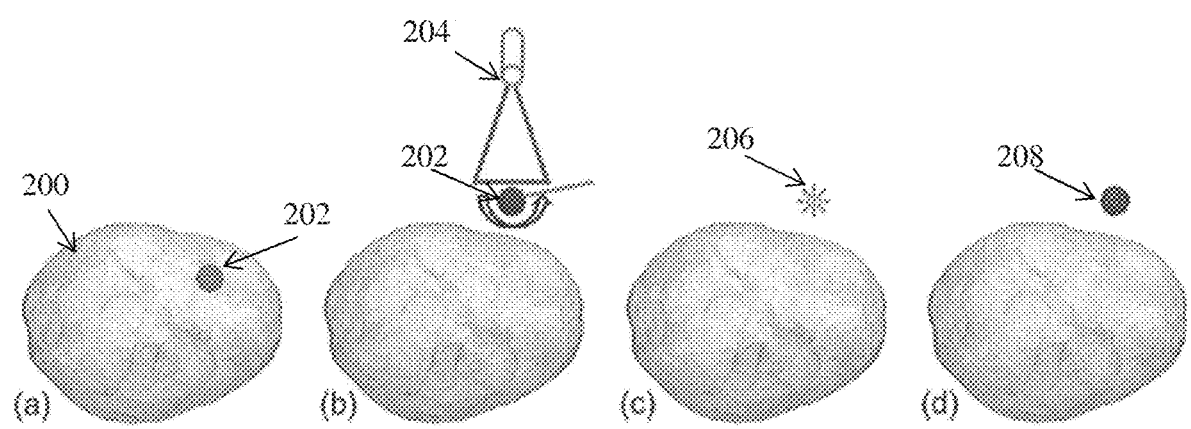
FIG. 2 illustrates exemplary results for the method steps of FIG. 1.

At step 102, tissue is resected in a surgical intervention. Resection refers to the removal of part of an organ or other body structure. For example, a surgical intervention can be performed to resect a tumor located in a soft-tissue organ, such as the brain, liver, lungs, etc. Accordingly, in an exemplary implementation, the resected tissue is tissue corresponding to a tumor that has been removed from an organ in a patient's body. FIG. 2 illustrates exemplary results for the method steps of FIG. 1. As shown in image (a) of FIG. 2, the resected tissue 202 is a tumor that removed from the brain 200.

At step 104, a stream of 2D/2.5D intraoperative images of the resected tissue is received. The intra-operative image stream can also be referred to as a video, with each frame of the video being an intra-operative image. For example, the intra-operative image stream can be a laparoscopic image stream acquired via a laparoscope, endoscopic image stream acquired via an endoscope, or a stream of intraoperative images acquired using a surgical microscope. According to an advantageous embodiment, each frame of the intra-operative image stream is a 2D/2.5D image. That is, each frame of the intra-operative image sequence includes a 2D image channel that provides 2D image appearance information for each of a plurality of pixels and a 2.5D depth channel that provides depth information corresponding to each of the plurality of pixels in the 2D image channel. For example, each frame of the intra-operative image sequence can be an RGB-D (Red, Green, Blue+Depth) image, which includes an RGB image, in which each pixel has an RGB value, and a depth image (depth map), in which the value of each pixel corresponds to a depth or distance of the considered pixel from the camera center of the image acquisition device (e.g., laparoscope, endoscope, or surgical microscope). The intra-operative image acquisition device (e.g., laparoscope, endoscope, or surgical microscope) used to acquire the intra-operative images can be equipped with a camera or video camera to acquire the RGB image for each time frame, as well as a time of flight or structured light sensor to acquire the depth information for each time frame.

The stream of the intraoperative images is acquired by aiming the intraoperative image acquisition device at the resected tissue and varying the angle of the intraoperative image acquisition device with respect to the surface of the resected tissue to such that the resected tissue is visualized from different angles in different ones of the intraoperative images (frames). In an advantageous embodiment, the stream of intraoperative images corresponds to a scan of the complete surface of the resected tissue by the intraoperative image acquisition device. Once the resected tissue is removed from the patient's body, the stream of intraoperative images may be acquired either by keeping the resected tissue is a fixed position and rotating the intraoperative image acquisition device with respect to the resected tissue, or by keeping the intraoperative image acquisition device at a fixed position and rotating the resected tissue with respect to the intraoperative image acquisition device. For example, as shown in image (b) of FIG. 2, the resected tissue 202 is removed from the brain 200, held in a field of view of an intraoperative image acquisition device 204 and rotated with respect to the intraoperative image acquisition device 204. In a possible implementation, the rotation of the resected tissue or the intraoperative image acquisition device may be performed manually by a user (e.g., physician). In this case the user can hold the resected tissue using forceps or some other surgical tool that obstructs the view of the resected tissue as little as possible. In another possible implementation, the rotation of the resected tissue or the intraoperative image acquisition device may be performed with robotic assistance. For example, once the resected tissue is removed from the patient's body, the resected tissue can be placed at the end of a robotic arm, which holds the resected tissue in the field of view of the intraoperative image acquisition device. The intraoperative image acquisition device remains in a fixed position, and the robotic arm rotates the resected tissue at a predetermined rate. The frames of the intraoperative image stream may be received directly from the image acquisition device. For example, in an advantageous embodiment, the frames of the intra-operative image stream can be received in real-time as they are acquired by the intra-operative image acquisition device. Alternatively, the frames of the intra-operative image sequence can be received by loading previously acquired intra-operative images of the resected tissue stored on a memory or storage of a computer system.

At step 106, the resected tissue surface is segmented in the 2D/2.5D intraoperative images. In order for the volume of the resected tissue to be calculated, the resected tissue must be segmented from the rest of the scene in the intraoperative images. Accordingly, binary image segmentation can be performed on each 2D/2.5 intraoperative image (frame) to distinguish the resected tissue (foreground) from the rest of the intraoperative image (background).

In a first embodiment, the resected tissue in each intra-operative image is segmented using the depth values captured in the 2D/2.5D intraoperative image. In this embodiment, the resected tissue is physically lifted from the remaining tissue and is kept spatially separated from other structures during the acquisition of the intraoperative images. For example the resected tissue can be held (e.g., using forceps or another surgical tool, or on a robotic arm) above the remaining tissue. Since the tissue is lifted from the remaining tissue, the surface of the resected tissue is geometrically separated from the rest of the scene in the intraoperative image by sharp discontinuities visible in the depth information. These discontinuities are used to perform automated figure-ground segmentation between the resected tissue and remaining tissue in the intraoperative image. In an advantageous implementation, this automated segmentation approach assumes that the resected tissue is centered in the image center during image collection, and segments the surface of the resected tissue in the intraoperative image by searching for large depth discontinuities as the distance from the center of the intraoperative image increases. For example, a 3D point flow algorithm based on the distance and depth continuities can be used to extract the resected tissue surface in each intraoperative image. In addition, a machine-learning based classifier technique can be integrated the automated resected tissue segmentation to separate tool information from the resected tissue for improved volume estimation. Since a tool is used to hold the resected tissue, the tool may have similar depth values as the resected tissue in the intraoperative image. A machine-learning based classifier (e.g., Probabilistic Boosting tree (PBT) classifier) can be trained using annotated training images to detect the tool based on features extracted from the RGB and/or depth image channels in the intraoperative images. The detected tool can then be automatically removed from the segmented resected tissue surface.

In a second embodiment, the resected tissue in each intraoperative image is segmented using appearance driven segmentation based on a homogenous background. In this embodiment, the intraoperative images are acquired with the resected tissue placed on a surface with a homogenous background and the homogenous background is used for automated tissue segmentation is 3D space. The 2D/2.5D intraoperative images provide multi-view appearance as well as geometric information. Prior information, such as the background color and shape of the flat background, is integrated and used to automate the binary tissue segmentation in the intraoperative images. In particular, the segmentation can be implemented based on the prior knowledge of the homogenous background and the color (RGB) information in the intraoperative image using various well known segmentations techniques, such as machine-learning based segmentation, region growing, graph cuts, etc.

At step 108, the segmented resected tissue surfaces are stitched to generate a 3D point cloud representation of the full resected tissue surface. Due to the availability of the resected tissue segmentation in the intraoperative images (step 106), only the resected tissue is reconstructed/stitched in 3D space. According to an advantageous implementation, the 3D reconstruction (stitching) is performed as follows. First, correspondences are estimated between the segmented resected tissue surfaces in individual frames are estimated using the RGB image data. The segmented resected tissue surfaces in individual frames are compared using the image measurements in the RGB channel to estimate corresponding frames with overlapping regions of the segmented resected tissue surface. Next, a robust pose estimation is performed to estimate relative poses between the individual frames. The relative poses between corresponding frames can be estimated based on the corresponding image measurements and/or based on the corresponding depth measurements. A global bundle adjustment step is then performed to optimize the 3D structure of the resected tissue surface. In particular, the bundle adjustment optimizes the final geometric structure of the resected tissue by adjusting the set of estimated relative poses between the individual frames, as well as original camera poses associated with the frames, with respect to an error metric defined in the 2D image domain by minimizing a 2D re-projection error in pixel space or in metric defined in 3D space where a 3D distance is minimized between corresponding 3D points of the resected tissue surface. Together with the 2.5D depth channel information, the estimated poses are used to stitch the segmented resected tissue surfaces in the 2D/2.5D intraoperative images into a consistent 3D point cloud model of the resected tissue. Image (c) of FIG. 2 shows a 3D point cloud representation 206 of the resected tissue 202.

At step 110, a 3D mesh representation of the resected tissue surface is generated from the 3D point cloud representation of the resected tissue surface. Once a 3D point cloud representing a surface description of the resected tissue is constructed using the stitching process, the 3D point cloud converted to a 3D mesh representation so that its volume can be calculated. A meshing technique is applied to the 3D point cloud representation to generate a closed 3D mesh of the resected tissue surface. For example, such a meshing technique may perform a triangulation procedure on the 3D point cloud to connect the points of the 3D point cloud with a smooth surface, and then fill in this surface with polygonal (e.g., tetrahedral, hexahedral, etc.) mesh elements. Since visibility information is available for each of the 3D measurements (i.e., 3D point normals of the with respect to camera view vectors), standard well known meshing techniques, such as Poisson triangulation or marching cubes, can be applied to the 3D point cloud to generate a smooth watertight (closed) 3D mesh. In an exemplary implementation, Poisson triangulation is used to generate the 3D mesh, as this technique preserves smooth surfaces, which is relevant in consistent 3D modeling of natural structures. Depending on the data collection and segmentation strategies, the meshing technique may utilize information such as the background surface or one or more tumor shape priors to increase the accuracy of the closed 3D mesh surface generated for the resected tissue. For example, shape priors of the tumor extracted from preoperative imaging data, such as preoperative computed tomography (CT), or magnetic resonance (MR) images of the patient, can be use to constrain the construction of the 3D mesh. Image (d) of FIG. 2 shows a 3D mesh representation 208 of the resected tissue 202.

At step 112, a volume of the resected tissue is estimated from the 3D mesh representation of the resected tissue surface. In particular, the volume of the resected tissue is calculated as the volume of the 3D mesh representation of the resected tissue surface. In one embodiment, in the case in which the 3D mesh representation of the resected tissue surface is a polygonal mesh, the volume of the 3D mesh can be calculated by integrating the volumes of the individual polygonal (e.g., tetrahedral, hexagonal, etc.) mesh elements over all of the mesh elements in the 3D mesh. In another embodiment, since the 3D mesh representation is a watertight (closed) surface mesh, the divergence theorem algorithm can be used to calculate the volume. In this case, the volume is estimated from a pointlist of points on the mesh surface as:

$$V = k_x \Sigma_i (x_i n_{x_i} \Delta a_i) + k_y \Sigma_i (y_i n_{y_i} \Delta a_i) + k_z \Sigma_i (z_i n_{z_i} \Delta a_i),$$

where i refers to a mesh point on the 3D surface mesh, $x_i$, $y_i$, and $z_i$ are coordinates of point i, $n_{x_i}$, $n_{y_i}$, and $n_{z_i}$ are unit normal vector components at point i, $\Delta a_i$ is a differential surface area at point i, and $k_x$, $k_y$, and $k_z$ are coefficients whose sum is equal to one. The coefficients $k_x$, $k_y$, and $k_z$ are calculated as a fraction of the total number of points in which the maximum unit vector of those points' gradient vector was in the direction of the subscript of the coefficient. The calculated volume measurement of the resected image is output, for example by displaying the volume measurement (e.g., in $cm^3$ or any other unit of volume) on a display device of computer system or storing the volume measurement is a storage or memory of a computer system.

In a possible embodiment, a target volume can be determined based on preoperative medical imaging data (e.g., CT or MR image data). For example, a tumor to be resected can be detected in the preoperative medical imaging data and a volume of the tumor can be estimated based on the preoperative medical image data. The volume measurement calculated from the 3D mesh representation of the resected tissue can then be compared to the target volume to determine if the resection successfully removed the entire tumor.

As described above, the volume measurement of the resected tissue is output. The intraoperative images received in step 104 of FIG. 1 can also be output, for example by displaying the intraoperative images on a display device. For example, the stream of intraoperative image can be output as a video on a display device. The segmented resected tissue surfaces resulting from the binary segmentation of the intraoperative images in step 106 of FIG. 1, the 3D point cloud representation of the resected tissue surface generated in step 108 of FIG. 1, and/or the 3D mesh representation of the resected tissue surface generated in step 110 of FIG. 1 can also be output, for example by displaying the results of these steps on a display device of a computer system.

Figure 3:
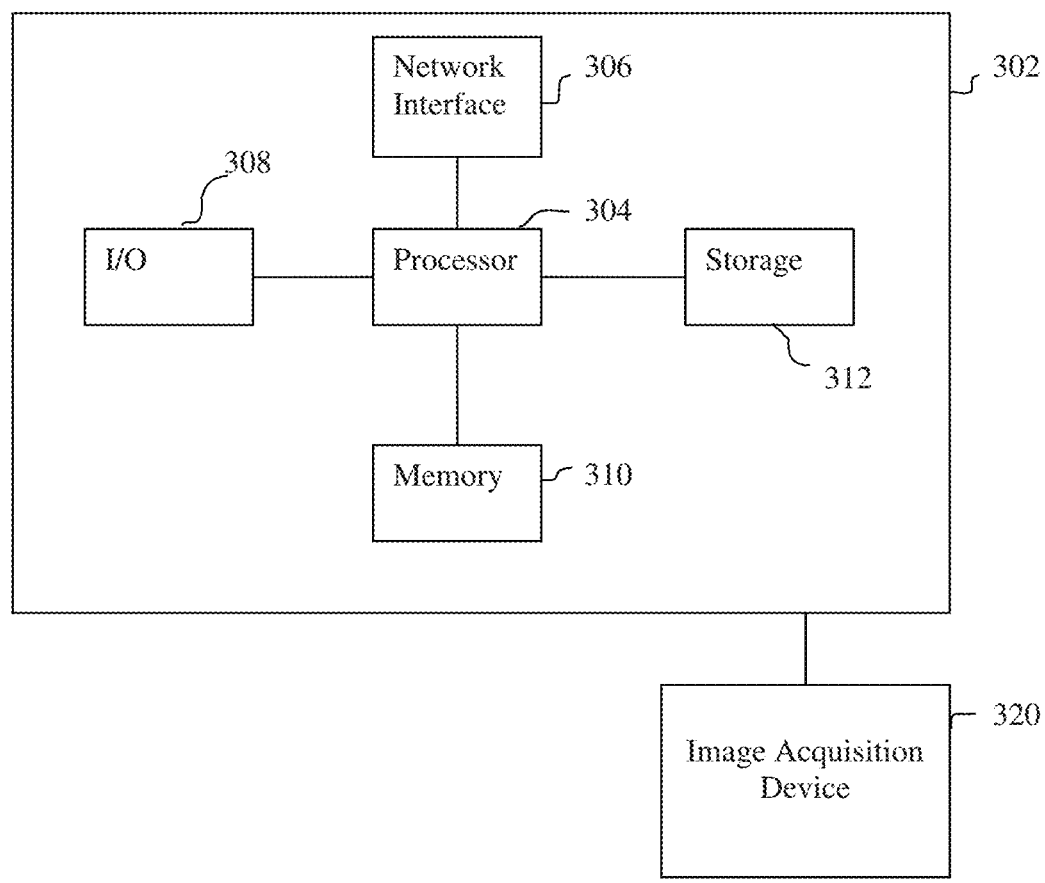
FIG. 3 is a high-level block diagram of a computer capable of implementing the present invention.

The above-described method for calculating a volume of resected tissue from 2D/2.5D intraoperative image data may be implemented on a computer using well-known computer processors, memory units, storage devices, computer software, and other components. A high-level block diagram of such a computer is illustrated in FIG. 3. Computer 302 contains a processor 304, which controls the overall operation of the computer 302 by executing computer program instructions which define such operation. The computer program instructions may be stored in a storage device 312 (e.g., magnetic disk) and loaded into memory 310 when execution of the computer program instructions is desired. Thus, the steps of the method of FIG. 1 may be defined by the computer program instructions stored in the memory 310 and/or storage 312 and controlled by the processor 304 executing the computer program instructions. An intraoperative image acquisition device 320, such as a laparoscope, endoscope, or surgical microscope, can be connected to the computer 302 to input image data to the computer 302. It is possible that the image acquisition device 320 and the computer 302 communicate wirelessly through a network.

The computer 302 also includes one or more network interfaces 306 for communicating with other devices via a network. The computer 302 also includes other input/output devices 308 that enable user interaction with the computer 302 (e.g., display, keyboard, mouse, speakers, buttons, etc.). Such input/output devices 308 may be used in conjunction with a set of computer programs as an annotation tool to annotate volumes received from the image acquisition device 320. One skilled in the art will recognize that an implementation of an actual computer could contain other components as well, and that FIG. 3 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for calculating a volume of resected tissue from a stream of intraoperative images, comprising:
receiving a stream of 2D/2.5D intraoperative images of resected tissue of a patient that has been removed from surrounding tissue of the patient, wherein the stream of 2D/2.5D intraoperative images comprises a plurality of 2D/2.5D intraoperative images acquired at different angles with respect to the resected tissue, each of the plurality of 2D/2.5D intraoperative images comprising a 2D image channel and a 2.5D depth channel;
segmenting a resected tissue surface in each of the plurality of 2D/2.5D intraoperative images;
stitching the segmented resected tissue surfaces to generate a 3D point cloud representation of the resected tissue surface based on overlapping surfaces in the segmented resected tissue surfaces;
generating a 3D mesh representation of the resected tissue surface from the 3D point cloud representation of the resected tissue surface; and
calculating a volume of the resected tissue from the 3D mesh representation of the resected tissue surface.

2. The method of claim 1, wherein receiving a stream of 2D/2.5D intraoperative images of resected tissue of a patient that has been removed from surrounding tissue of the patient comprises:
acquiring the stream of 2D/2.5D intraoperative images of the resected tissue by rotating the resected tissue in a field of view of a stationary intraoperative image acquisition device.

3. The method of claim 2, wherein the resected tissue is rotated by a robotic arm during the acquisition of the stream of 2D/2.5D intraoperative images.

4. The method of claim 1, wherein receiving a stream of 2D/2.5D intraoperative images of resected tissue of a patient that has been removed from surrounding tissue of the patient comprises:
acquiring the stream of 2D/2.5D intraoperative images of the resected tissue by rotating an intraoperative image acquisition device around the resected tissue.

5. The method of claim 1, wherein the stream of 2D/2.5D intraoperative images is acquired with the resected tissue in a lifted positon with respect to the surrounding tissue and segmenting a resected tissue surface in each of the plurality of 2D/2.5D intraoperative images comprises:
segmenting the resected tissue surface in each of the plurality of 2D/2.5D intraoperative images based on discontinuities in depth measurements in a depth channel of each of the plurality of 2D/2.5D intraoperative images.

6. The method of claim 5, wherein segmenting a resected tissue surface in each of the plurality of 2D/2.5D intraoperative images further comprises:
detecting a tool holding the resected tissue in each of the plurality of 2D/2.5D intraoperative images using a trained machine-learning based classifier; and
removing the detected tool from the segmented resected tissue surface in each of the plurality of 2D/2.5D intraoperative images.

7. The method of claim 1, wherein the stream of 2D/2.5D intraoperative images is acquired with the resected tissue on a homogenous background and segmenting a resected tissue surface in each of the plurality of 2D/2.5D intraoperative images comprises:
segmenting the resected tissue in each of the plurality of 2D/2.5D intraoperative images based on a color of the homogenous background and color measurements in an image channel of each of the plurality of 2D/2.5D intraoperative images.

8. The method of claim 1, wherein stitching the segmented resected tissue surfaces to generate a 3D point cloud representation of the resected tissue surface based on overlapping surfaces in the segmented resected tissue surfaces comprises:
estimating correspondences of the overlapping surfaces between pairs of the segmented resected tissue surfaces in the plurality of 2D/2.5D intraoperative images;
reconstructing relative 3D poses between the segmented resected tissue surfaces in the plurality of 2D/2.5D intraoperative images based on the estimated correspondences; and
adjusting the relative 3D poses between the segmented resected tissue surfaces using a global bundle adjustment to optimize a 3D structure of the 3D point cloud representation generated using the relative 3D poses between the segmented resected tissue surfaces.

9. The method of claim 1, wherein generating a 3D mesh representation of the resected tissue surface from the 3D point cloud representation of the resected tissue surface comprises:
generating smooth surface by triangulating points in the 3D point cloud representation of the resected tissue surface; and
fitting a plurality of polygonal mesh elements to the smooth surface, resulting in a closed 3D mesh.

10. The method of claim 1, wherein generating a 3D mesh representation of the resected tissue surface from the 3D point cloud representation of the resected tissue surface comprises:
generating the 3D mesh representation of the resected tissue surface subject to a shape prior constraint based on a shape prior extracted from preoperative medical imaging data of the patient.

11. The method of claim 1, wherein the 3D mesh representation of the resected tissue surface is a polygonal mesh and calculating a volume of the resected tissue from the 3D mesh representation of the resected tissue surface comprises:

integrating volumes of individual polygonal mesh elements over all of the polygonal mesh elements of the 3D mesh representation of the resected tissue surface.

12. The method of claim 1, wherein calculating a volume of the resected tissue from the 3D mesh representation of the resected tissue surface comprises:
calculating the volume of the 3D mesh representation of the resected tissue surface based on a pointlist of mesh point of the 3D mesh representation of the resected tissue surface using a divergence theorem algorithm.

13. An apparatus for calculating a volume of resected tissue from a stream of intraoperative images, comprising:
a processor; and
a memory to store computer program instructions, the computer program instructions when executed on the processor cause the processor to perform operations comprising:
acquiring a stream of 2D/2.5D intraoperative images of resected tissue of a patient that has been removed from surrounding tissue of the patient, wherein the stream of 2D/2.5D intraoperative images comprises a plurality of 2D/2.5D intraoperative images acquired at different angles with respect to the resected tissue, each of the plurality of 2D/2.5D intraoperative images comprising a 2D image channel and a 2.5D depth channel;
segmenting a resected tissue surface in each of the plurality of 2D/2.5D intraoperative images;
stitching the segmented resected tissue surfaces to generate a 3D point cloud representation of the resected tissue surface based on overlapping surfaces in the segmented resected tissue surfaces;
generating a 3D mesh representation of the resected tissue surface from the 3D point cloud representation of the resected tissue surface; and
calculating a volume of the resected tissue from the 3D mesh representation of the resected tissue surface.

14. The apparatus of claim 13, wherein the stream of 2D/2.5D intraoperative images is acquired with the resected tissue in a lifted positon with respect to the surrounding tissue and segmenting a resected tissue surface in each of the plurality of 2D/2.5D intraoperative images comprises:
segmenting the resected tissue surface in each of the plurality of 2D/2.5D intraoperative images based on discontinuities in depth measurements in a depth channel of each of the plurality of 2D/2.5D intraoperative images.

15. The apparatus of claim 13, wherein the stream of 2D/2.5D intraoperative images is acquired with the resected tissue on a homogenous background and segmenting a resected tissue surface in each of the plurality of 2D/2.5D intraoperative images comprises:
segmenting the resected tissue in each of the plurality of 2D/2.5D intraoperative images based on a color of the homogenous background and color measurements in an image channel of each of the plurality of 2D/2.5D intraoperative images.

16. The apparatus of claim 13, wherein stitching the segmented resected tissue surfaces to generate a 3D point cloud representation of the resected tissue surface based on overlapping surfaces in the segmented resected tissue surfaces comprises:
estimating correspondences of the overlapping surfaces between pairs of the segmented resected tissue surfaces in the plurality of 2D/2.5D intraoperative images;
reconstructing relative 3D poses between the segmented resected tissue surfaces in the plurality of 2D/2.5D intraoperative images based on the estimated correspondences; and
adjusting the relative 3D poses between the segmented resected tissue surfaces using a global bundle adjustment to optimize a 3D structure of the 3D point cloud representation generated using the relative 3D poses between the segmented resected tissue surfaces.

17. The apparatus of claim 13, wherein calculating a volume of the resected tissue from the 3D mesh representation of the resected tissue surface comprises:
estimating a volume of the 3D mesh representation of the resected tissue surface.

18. A non-transitory computer readable medium storing computer program instructions for calculating a volume of resected tissue from a stream of intraoperative images, the computer program instructions, when executed by a processor cause the processor to perform operations comprising:
receiving a stream of 2D/2.5D intraoperative images of resected tissue of a patient that has been removed from surrounding tissue of the patient, wherein the stream of 2D/2.5D intraoperative images comprises a plurality of 2D/2.5D intraoperative images acquired at different angles with respect to the resected tissue, each of the plurality of 2D/2.5D intraoperative images comprising a 2D image channel and a 2.5D depth channel;
segmenting a resected tissue surface in each of the plurality of 2D/2.5D intraoperative images;
stitching the segmented resected tissue surfaces to generate a 3D point cloud representation of the resected tissue surface based on overlapping surfaces in the segmented resected tissue surfaces;
generating a 3D mesh representation of the resected tissue surface from the 3D point cloud representation of the resected tissue surface; and
calculating a volume of the resected tissue from the 3D mesh representation of the resected tissue surface.

19. The non-transitory computer readable medium of claim 18, wherein the stream of 2D/2.5D intraoperative images is acquired with the resected tissue in a lifted positon with respect to the surrounding tissue and segmenting a resected tissue surface in each of the plurality of 2D/2.5D intraoperative images comprises:
segmenting the resected tissue surface in each of the plurality of 2D/2.5D intraoperative images based on discontinuities in depth measurements in a depth channel of each of the plurality of 2D/2.5D intraoperative images.

20. The non-transitory computer readable medium of claim 19, wherein segmenting a resected tissue surface in each of the plurality of 2D/2.5D intraoperative images further comprises:
detecting a tool holding the resected tissue in each of the plurality of 2D/2.5D intraoperative images using a trained machine-learning based classifier; and
removing the detected tool from the segmented resected tissue surface in each of the plurality of 2D/2.5D intraoperative images.

21. The non-transitory computer readable medium of claim 18, wherein the stream of 2D/2.5D intraoperative images is acquired with the resected tissue on a homogenous background and segmenting a resected tissue surface in each of the plurality of 2D/2.5D intraoperative images comprises:
segmenting the resected tissue in each of the plurality of 2D/2.5D intraoperative images based on a color of the homogenous background and color measurements in an image channel of each of the plurality of 2D/2.5D intraoperative images.

22. The non-transitory computer readable medium of claim 18, wherein stitching the segmented resected tissue surfaces to generate a 3D point cloud representation of the resected tissue surface based on overlapping surfaces in the segmented resected tissue surfaces comprises:

estimating correspondences of the overlapping surfaces between pairs of the segmented resected tissue surfaces in the plurality of 2D/2.5D intraoperative images;

reconstructing relative 3D poses between the segmented resected tissue surfaces in the plurality of 2D/2.5D intraoperative images based on the estimated correspondences; and adjusting the relative 3D poses between the segmented resected tissue surfaces using a global bundle adjustment to optimize a 3D structure of the 3D point cloud representation generated using the relative 3D poses between the segmented resected tissue surfaces.

23. The non-transitory computer readable medium of claim 18, wherein generating a 3D mesh representation of the resected tissue surface from the 3D point cloud representation of the resected tissue surface comprises:

generating smooth surface by triangulating points in the 3D point cloud representation of the resected tissue surface; and fitting a plurality of polygonal mesh elements to the smooth surface, resulting in a closed 3D mesh.

24. The non-transitory computer readable medium of claim 18, wherein the 3D mesh representation of the resected tissue surface is a polygonal mesh and calculating a volume of the resected tissue from the 3D mesh representation of the resected tissue surface comprises:

integrating volumes of individual polygonal mesh elements over all of the polygonal mesh elements of the 3D mesh representation of the resected tissue surface.

25. The non-transitory computer readable medium of claim 18, wherein calculating a volume of the resected tissue from the 3D mesh representation of the resected tissue surface comprises:

calculating the volume of the 3D mesh representation of the resected tissue surface based on a pointlist of mesh point of the 3D mesh representation of the resected tissue surface using a divergence theorem algorithm.

\* \* \* \* \*